US008507697B2

(12) United States Patent
Dhainaut et al.

(10) Patent No.: US 8,507,697 B2
(45) Date of Patent: Aug. 13, 2013

(54) PHOTOCHEMICAL PROCESS FOR PRODUCING ARTEMISININ

(75) Inventors: Jildaz Dhainaut, Paris (FR); Alain Dlubala, Paris (FR); Ronan Guevel, Paris (FR); Alain Medard, Paris (FR); Gilles Oddon, Paris (FR); Nicolas Raymond, Paris (FR); Joel Turconi, Paris (FR)

(73) Assignee: Sanofi, Paris (FR)

( * ) Notice: Subject to any disclaimer, the term of this patent is extended or adjusted under 35 U.S.C. 154(b) by 7 days.

(21) Appl. No.: 12/873,925

(22) Filed: Sep. 1, 2010

(65) Prior Publication Data

US 2011/0065933 A1 Mar. 17, 2011

(30) Foreign Application Priority Data

Sep. 1, 2009 (EP) .................................. 09305805

(51) Int. Cl.
*C07D 311/78* (2006.01)
(52) U.S. Cl.
USPC ......................................................... 549/276
(58) Field of Classification Search
USPC ......................................................... 549/276
See application file for complete search history.

(56) References Cited

U.S. PATENT DOCUMENTS

| 4,992,561 A | 2/1991 | Roth et al. |
| 5,872,273 A | 2/1999 | Saito et al. |
| 5,955,084 A | 9/1999 | Jain et al. |
| 6,313,317 B1 | 11/2001 | Sayo et al. |

FOREIGN PATENT DOCUMENTS

| IN | 184682 | 9/2000 |
| WO | WO 2006/128126 | 11/2006 |
| WO | WO 2009/088404 A1 | 7/2009 |

OTHER PUBLICATIONS

Imada et al., "Flavin-Catalyzed Generation of Diimide: An Environmentally Friendly Method for the Aerobic Hydrogenation of Olefins," *Journal of the American Chemical Society*, 2005, vol. 127, No. 42, pp. 14544-14545.
International Search Report and Written Opinion of the International Searching Authority for PCT/IB2010/002566 mailed on Mar. 16, 2011.
International Search Report and Written Opinion mailed on Dec. 9, 2010, for International Application No. PCT/EP2010/062811, filed on Sep. 1, 2010.

European Seach Report dated Feb. 9, 2010, issued in European Application No. 09305805.5, 5 pages.
Liu, H. et al., "A Total Synthesis of the Antimalarial Natural Product (+)-Qinghaosu," *Tetrahedron Letters*, vol. 34, No. 28, pp. 4435-4438 (1993), XP-002565213.
Abdin et al., Artemisinin, a novel antimalarial drug: biochemical and molecular approaches for enhanced production. *Planta Med* 2003, 69(4), 289-99.
Greene et al., Protective Groups in Organic synthesis; Wiley-Interscience 3$^{rd}$ ed., chapter 5 (1999).
Jung et al., A concise and stereoselective Synthesis of (+)-12-butyldeoxoartemisinin, *Synlett* 1990, 12, 743-744.
Miyashita et al., Synthesis of 2,2'-bis(diphenylphosphino)-1,1'-binapthyl(BINAP), an atropisomeric chiral bis(triaryl)phosphine, and its use in the rhodium(I)-catalyzed asymmetric hydrogenation of α-(acylamino)acrylic acids. *J. Am. Chem. Soc.* 1980, 102(27), 7932-7934.
Pasto and Taylor, Reduction with diimide. L.A. Paquette, Editor, Organic Reactions vol. 40, John Willey and Sons, Inc., New York (1991), pp. 91-155.
Lenihan et al., Developing an industrial artemisinic acid fermentation process to support the cost-effective production of antimalarial artemisinin-based combination therapies. *Biotechnol Prog.* 2008, 24(5), 1026-32.
Ro et al., Production of the antimalarial drug precursor artemisinic acid in engineered yeast. *Nature* 2006, 440(7086), 940-3.
Roth et al., Isolation of arteannuic acid from *Artemisia annua*. *Planta Med* 1987, 53(5), 501-2.
Schmid and Hofheinz, Total synthesis of qinghaosu. *J. Am. Chem. Soc.* 1983, 105, 624-625.
Wallaart et al., Seasonal variation of artemisinin and its biosynthetic precursors in plants of *Artemisia annua* of different geographical origin: proof for the existence of chemotypes. *Planta Med* 2000, 66(1), 57-62.
Wei-Shan et al., Studies on the structures and synthesis of arteannuin and related compounds: XVI. Synthesis of arteannuin E and epoxy fission reaction of methyl α-epoxy arteannuinate. *HuexueXuebao (Acta Chimica Sinica)* 1985, 43(9), 845-851.
Xu et al., Total synthesis of arteannuin and deoxyarteannuin. *Tetrahedron* 1986, 42(3), 819-828.
European Search Report dated Feb. 9, 2010, issued in European Application No. 09305805.5, 5 pages.
U.S. Appl. No. 12/879,241, filed Sep. 20, 2010.
Bentley et al., "Kinetic and spectroscopic characterisation of highly reactive methanesulfonates. Leaving group effects for solvolyses and comments on geminal electronic effects influencing $S_N1$ reactivity," *J. Chem. Soc., Perkin Trans.* 2: 2531-2538 (1994).
Kaboudin, "Preparation of Acyl Phosphates on the Surface of Magnesia," *Synthetic Communications*, 32(4): 637-640 (2002).
Milas et al., "Studies in Organic Peroxides. IX. *t*-Butyl Peresters," *J. Chem. Soc.* 68: 642-43 (1946).
Smith et al., *March's Advanced Organic Chemistry: Reactions, Mechanisms, and Structure*, 6th ed., pp. 496-502, John Wiley & Sons, Hoboken, NJ (2006).

*Primary Examiner* — Nizal Chandrakumar
(74) *Attorney, Agent, or Firm* — Finnegan, Henderson, Farabow, Garrett & Dunner, LLP

(57) ABSTRACT

Provided is a new photochemical process for preparing artemisinin. Also provided are certain dihydroartemisinic acid derivatives useful for preparing artemisinin.

17 Claims, No Drawings

PHOTOCHEMICAL PROCESS FOR PRODUCING ARTEMISININ

This application claims benefit of priority under 35 U.S.C. §119 to European Patent Application No. 09305805.5, filed Sep. 1, 2009.

The inventors provide a new photochemical process for preparing artemisinin as well as certain dihydroartemisinic acid derivatives useful for preparing artemisinin.

Artemisinin, a therapeutically active component of the traditional Chinese drug Qinghao (*Artemisia annua* L.), is a sesquiterpenoid lactone bearing a peroxy group. The chemical structure of artemisinin is shown in the following formula (A):

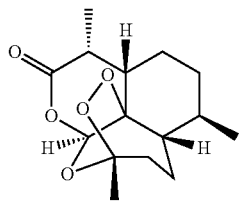

(A)

Artemisinin not only has an excellent antimalarial effect, but has also an effective anti-parasitic activity towards other parasites such as *Schistosoma japonicum* etc. Moreover artemisinin has been found to be immunosuppressive, and was once used in a clinical trial for treating lupus erythematosus with promising results. With the extension of related research work, it has been found that artesunate, a derivative of artemisinin, has a stronger immunosuppressive activity than artemisinin. It may achieve better therapeutic effects in the treatment of lupus erythematosus and some skin diseases.

From some studies, it appears that artemisinin or its derivatives may play a role in the treatment of cancer.

Artemisinin is thus a useful compound, and a need exists for an easy process for the preparation thereof.

Different synthetic pathways are disclosed in the literature, where dihydroartemisinic acids (DHAA) of formula (B)

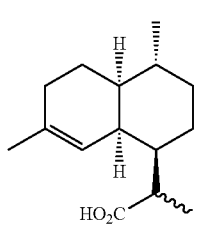

(B)

or DHAA derivatives, in particular esters thereof, are used as starting compounds (Tetrahedron 2002 (58), 909-923). These DHAA derivatives are used in a method comprising, among other steps, their photooxidation with a photosensitizer. Further transformations occur, in order to provide artemisinin. In particular allylic hydroperoxides obtained after the photooxidation undergo rearrangement in a polar aprotic solvent.

A diastereoisomer of DHAA is represented by formula (B1)

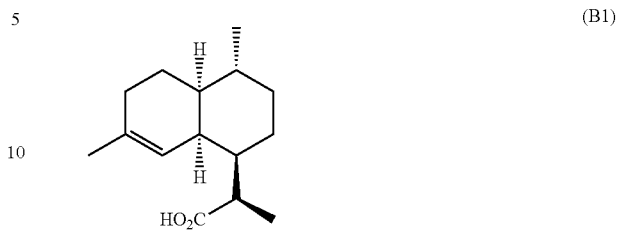

(B1)

A process where photochemical oxidation is used at an early stage to obtain a synthetic intermediate (compound 4) of artemisinin in the $3^{rd}$ step of a process comprising 16 steps is disclosed in Tetrahedron Letters, 1993 (34), 4435-4438. This document also discloses methyl esters of DHAA used at the end of the process.

However, the prior synthetic processes starting from DHAA or methyl esters of DHAA have, in particular, the following drawbacks:

the preparation of DHAA ester with classical methods is less effective or needs the use of costly or unsafe reagents;

the artemisinin finally obtained from DHAA or esters thereof is not stable because of the presence in the medium of by-products obtained through secondary reactions, such as ring opening, when carrying out the process; and the yield of artemisinin obtained is low.

Also, the methods disclosed in the literature involve numerous steps which may render them inapplicable to industrial scale.

It has now been found that, by using dihydroartemisinic acid derivatives where the carboxylic acid function is activated through specific activating groups, it may be possible to obtain artemisinin by a one-pot photochemical process with a high yield, while significantly lowering the production costs.

It has been found that the use of these activating groups and of specifically designed reaction parameters may provide one or more of the following advantages:

the use of activated derivatives of DHAA as starting material may limit the formation of undesired by-products through interfering reactions, such as lactonisation;

the kinetics of the reaction may be increased when using these activated derivatives where activating groups are better leaving groups, in comparison to DHAA or esters thereof; and preparation of activated derivatives of DHAA may be a one step simple and quantitative procedure.

In order to achieve a suitable process for preparing artemisinin, prior art processes have been studied to analyse and quantify the undesired by-products obtained, in particular as regards the kinetics of their formation, in order to prevent their appearance and to favour the formation of artemisinin.

In this study, it was found that it was possible to control the formation of the different reaction intermediates by having the temperature gradually raised during the process. The starting product was converted into a first synthetic intermediate at a low temperature (below 0° C.), which then underwent a conversion into a second synthetic intermediate at 0° C. Raising the temperature up in a subsequent step allowed complete transformation of this second synthetic intermediate into artemisinin.

It was thus found that it was possible to optimize the process by using designed temperature levels in order to limit the formation of undesired by-products and to increase the yield in artemisinin.

This study made it possible to design a specific process for preparing artemisinin by combining reaction parameters such as, for example, temperature, time and sequence of synthetic steps ("one-pot" process).

Also, by adequately combining the reaction parameters, it is now possible to perform a "one pot" reaction process for obtaining artemisinin where two subsequent oxidation steps are linked together, which was not taught or suggested in the prior art.

Provided is a process for preparing artemisinin, comprising the steps of:
preparing a mixture comprising
(i) a dihydroartemisinic acid (DHAA) derivative of formula (I)

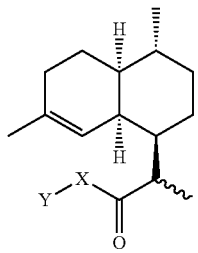

(I)

wherein
X is O, S, NH or NO
Y is a group selected from formulae (II), (III) and (IV)

(II)

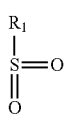

(III)

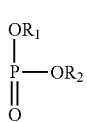

(IV)

or, when, X is O, Y can represent $OR_4$ $R_1$ and $R_2$, independently from each other, are hydrogen; a $C_1$-$C_{12}$ alkyl group which is linear or branched or a $C_3$-$C_{10}$ cycloalkyl group, said alkyl group being unsubstituted or substituted by one or more substituent(s) selected from a $C_1$-$C_6$ alkyl group and a halogen; a trifluoromethyl group; a cycloalkylalkyl group where cycloalkyl and alkyl are as defined above; a $C_2$-$C_{12}$ alkenyl group which is linear or branched, said alkenyl group being unsubstituted or substituted by one or more substituent(s) selected from a $C_1$-$C_6$ alkyl group and a halogen; a $C_5$-$C_{14}$ aryl or heteroaryl group, said aryl or heteroaryl group being unsubstituted or substituted by one or more substituent(s) selected from a $C_1$-$C_6$ alkyl group and a halogen; an arylalkyl group where aryl and alkyl are as defined above; or a heteroarylalkyl group where heteroaryl and alkyl are as defined above;

$R_3$ is $R_1$, $OR_1$, $NHR_1$ or $NR_1R_2$, where $R_1$ and $R_2$ are as defined above;

$R_4$ is identical to $R_1$, except that $R_4$ cannot represent hydrogen or else $R_4$ represents a silyl group;

(ii) at least one organic solvent and (iii) a photosensitizer, subjecting said mixture to photooxidation by means of a light source, and
recovering the artemisinin thus obtained.

In some embodiments, a DHAA derivative of formula (Ia)

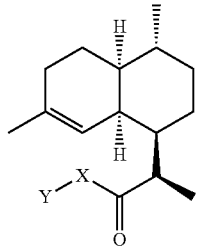

(Ia)

in which X and Y are as defined above, is used in the above process.

When a compound of formula (I) under racemic form is used in the above process, the diastereoisomer which does not have the stereochemistry of formula (Ia) can be separated from the reaction mixture after recovering artemisinin, by usual purification means, such as, for example, crystallization and filtering, while simultaneously separating any undesired by-product which may be present.

Alternatively, separation of the diastereoisomers can be performed prior to subjecting the reaction mixture to photooxidation, so that only the diastereoisomer of formula (Ia) is involved in the subsequent process steps.

According to the present description, organic solvent means an organic compound, i.e. comprising at least one carbon atom, used for solvating other substances.

Organic solvents include protic solvents and aprotic solvents, and may be polar or non polar.

Examples of suitable organic solvents are given here below.

A $C_1$-$C_{12}$ alkyl group which is linear or branched can be selected, for example, from methyl, ethyl, propyl, isopropyl, butyl, isobutyl, sec-butyl, tert-butyl, pentyl, isopentyl, sec-pentyl, tert-pentyl, neopentyl, hexyl, isohexyl, sec-hexyl, tert-hexyl, heptyl, octyl, nonyl, decyl, undecyl and dodecyl. In some embodiments, $C_1$-$C_6$ alkyl groups which are linear or branched can be selected.

A $C_3$-$C_{10}$ cycloalkyl group denotes a carbocyclic group which may comprise one or two rings, such as, for example, cyclopropyl, cyclobutyl, cyclopentyl or cyclohexyl.

A $C_2$-$C_{12}$ alkenyl group denotes a linear or branched hydrocarbon group containing one or more unsaturated bonds such as, for example, ethenyl or vinyl, propenyl or allyl, 1-propenyl, n-butenyl, i-butenyl, 3-methylbut-2-enyl, n-pentenyl, hexenyl, heptenyl, octenyl, decenyl. In some embodiments, $C_2$-$C_4$ alkenyl groups which are linear or branched can be selected.

A cycloalkylalkyl group denotes a group where cycloalkyl and alkyl are as defined above, such as, for example, cyclopropylmethyl, cyclobutylmethyl, cyclopentylmethyl, cyclohexylmethyl, cycloheptylmethyl, cyclopropylethyl or cyclohexylethyl.

A $C_5$-$C_{14}$ aryl group denotes an unsaturated carbocyclic group comprising one or two rings, such as, for example, phenyl, naphthyl, indenyl or anthracenyl. In some embodiments, the $C_5$-$C_{14}$ aryl group is phenyl.

An arylalkyl denotes a carbocyclic group where aryl and alkyl are as defined above, such as, for example, benzyl, phenylethyl, 2-phenylethyl or naphthylmethyl. In some embodiments, the arylalkyl is benzyl.

A $C_5$-$C_{14}$ heteroaryl group denotes an aromatic carbocyclic group comprising one, two or three rings, or a carbocyclic group comprising two rings where one ring is aromatic and the other is completely hydrogenated, or a carbocyclic group comprising three rings where at least one ring is aromatic and the other ring(s) is (are) completely hydrogenated, said carbocyclic ring comprising one or more heteroatoms, identical or different, selected from oxygen and nitrogen atoms, such as, for example, furyl, pyrrolyl, oxazolyl, oxadiazolyl, isoxazolyl, imidazolyl, pyrazolyl, pyridyl, pyrimidinyl, pyridazinyl, pyrazinyl, tetrazolyl, benzofuranyl, indolyl, purinyl, quinolyl, isoquinolyl, chromanyl and naphthyridinyl.

An heteroarylalkyl group denotes a group where heteroaryl and alkyl are as defined above.

Halogens can be selected from fluorine, chlorine, bromine and iodine atoms.

The at least one organic solvent used in the process described herein can be, for example, selected from:

alcohols, such as methanol, ethanol, isopropanol, butanol, 1,2-butanediol, 1-3-butanediol, glycol, etc.;

chlorinated solvents, such as dichloromethane, chloroform, dichloroethane, monochlorobenzene, dichlorobenzene, orthodichlorobenzene, etc.;

ketones, such as acetone, butanone, methylethylketone (MEK), methylisobutylketone (MiBK), methylisopropylketone (MiPK), cyclohexanone, etc.;

sulfoxides, such as dimethylsulfoxide, etc.;

sulfones, such as, sulfolane, etc.;

nitriles, such as acetonitrile, etc.;

N,N-disubstituted amines, such as dimethylformamide, etc.;

esters, such as ethylacetate, isopropylacetate, etc.;

nitrogenated heterocycles, such as pyridine, etc.;

ethers, such as diethylether, methyl tert-butylether (MTBE), methylcyclopentylether, tetrahydrofuran, 2-methyltetrahydrofuran, dimethoxyethane (glyme), diglyme, triglyme, etc.;

alkanes, such as n-heptane, n-hexane, cyclohexane, n-pentane, CMC (mixture of cyclohexane and methylcyclohexane), etc.;

aromatic solvents such as, for example, anisole or toluene, etc.;

and mixtures thereof.

In some embodiments, dichloromethane is used, in particular for safety reasons. In some embodiments, a mixture of organic solvents is used.

The above list is not exhaustive, and a person skilled in the field is able to select an appropriate organic solvent or mixture of organic solvents on the basis of his general knowledge.

In some embodiments, the at least one organic solvent is used in a ratio of about 4 to 20 volumes with respect to the dihydroartemisinic acid derivative of formula (I) or (Ia).

A photosensitizer is any donor molecule D that, when electronically excited by light—D*—may transfer its energy to an acceptor molecule A (for example, ground state oxygen). In the course of such a process, the donor molecule D* is deactivated and the excited state of the acceptor molecule (for example, singlet state oxygen) is produced: A*. Sensitizers are generally dyes, which absorb the visible light (see "Photochemical Technology" page 22-23 from A. M. Braun, M.-T. Maurette et E. Oliveros edition John Wiley and Sons, and "March's Advanced Organic Chemistry" page 316, Fifth Edition M. B. Smith and J. March Wiley).

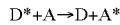

The photosensitizer can be, for example, selected from Rose bengal, tetraphenylporphyrin (TPP), tetraphenylporphyrin derivatives (TPP derivatives) such as, for example, metalloporphyrin, tetramethylthionine chloride (methylene blue), and toluidine blue. In some embodiments, Rose bengal or TPP is used. The photosensitizer can be used, for instance, in a molar ratio in the range of about 0.000001 to 1 equivalent with respect to the dihydroartemisinic acid derivative of formula (I) or (Ia), such as from 0.000004 to 0.0002 equivalents with respect to the dihydroartemisinic acid derivative of formula (I) or (Ia).

The light source can consist of any light source capable of emitting photons at the absorption wavelength of the photosensitizer. Such a light source can be, for example, selected from a halogen lamp, a mercury or nitrogen lamp, where mercury or nitrogen may be doped, a laser lamp, a diode lamp and natural light.

In some embodiments, halogen or mercury lamps are used.

The above list is not exhaustive, and a person skilled in the field is able to select an appropriate lamp on the basis of his general knowledge.

In some embodiments, the mixture comprises at least an acid catalyst, for example (i) at least a protic acid, such as, for example, triflic acid, acetic acid and trifluoroacetic acid, and/or (ii) at least a Lewis acid, such as, for instance $FeCl_3$, $Ln(OTf)_3$, $AlCl_3$, $SnCl_4$, $TiCl_4$ or $ZnCl_2$. In some embodiments, trifluoroacetic acid is used. In some embodiments, the acid catalyst may be present in an amount of from 0.5 to 2 equivalent(s) per equivalent of compound of formula (I) or (Ia).

In some embodiments, the process described herein may comprise the steps of:

preparing a mixture comprising (i) a dihydroartemisinic acid derivative of formula (I) or (Ia) as defined above, (ii) at least one organic solvent and (iii) a photosensitizer at ambient temperature, cooling the reaction mixture to a temperature in the range of about −78° C. to ambient temperature with air or oxygen bubbling into it, adding a catalytic amount of an acid catalyst, switching the light source on, maintaining the reaction mixture at the same temperature for 12 h to 24 h, warming up the reaction mixture to a temperature in the range of about 5 to 15° C. for 2 to 4 hours, and then to a higher temperature in the range of about 15 to 25° C. for 1 to 3 hours, stopping the reaction by means such as sequentially, in either sequence, or concurrently switching the light source off and stopping the air or oxygen bubbling, followed by adding a quencher at ambient temperatures, maintaining the reaction mixture at a temperature in the range of about 15° C. to 25° C. for 1 to 3 hours, and recovering artemisinin.

Ambient temperature is understood as being in the range of about 18 to 25° C.

Ranges are understood to include all points between and including the specified endpoints. For example, a temperature range of about 15 to 25° C. includes each and every temperature between about 15° C. and about 25° C. Likewise a range of time of 1 to 3 hours includes each and every time point between 1 and 3 hours.

In some embodiments, the reaction conditions are as follows:

the first cooling step is carried out at a temperature between −5° C. and −20° C., for example −10° C.;

during the warming up step, the reaction mixture is warmed up to 10° C. for 2 h, and then to ambient temperature, such as at 20° C. for 1 hour, and/or after stopping the reaction, the reaction mixture is maintained at ambient temperature, such as at 20° C. for 2 h.

In some embodiments after adding a catalytic amount of an acid catalyst and switching the light source on, the reaction mixture is maintained at ambient temperature for a period of 3 to 24 h. In some embodiments the time period is 3 to 12 hours. The time period may depend on the strength-power of light source, the amount of photosensitizer, and/or on the bubbling conditions.

In some embodiments, the acid catalyst is a protic acid which can be selected from the above-mentioned group. In some embodiments, the acid catalyst is trifluoroacetic acid.

In some embodiments before recovering artemisinin, the reaction mixture is treated with charcoal.

Artemisinin can be recovered in the final step by various means known to one of skill in the art. In some embodiments artemisinin can be recovered by crystallization and filtering.

In some embodiments artemisinin is recovered in the final step by precipitation and isolation in a solvent/alcohol mixture. In some embodiments the solvent/alcohol mixture is an alkane/alcohol mixture. In some embodiments the solvent is selected from n-heptane, n-hexane, cyclohexane, n-pentane, and CMC, and the alcohol is selected from ethanol and isopropanol. In some embodiments the ratio of alkane to alcohol is 10:1 (volume alkane/volume alcohol).

Optionally, an additional purification step can be performed in order to increase the purity of artemisinin. For instance, the recovered artemisinin may be precipitated in an appropriate solvent, such as, for instance, heptane (for example n-heptane), hexane (for example n-hexane or cyclohexane), pentane (for example n-pentane), and CMC and recrystallized in an alcohol/water mixture. In some embodiments the alcohol/water mixture is ethanol/water or ispropanol/water.

Artemisinin thus obtained has a high purity grade and the recrystallization yield is higher than 90%.

Also provided are compounds of formula (I)

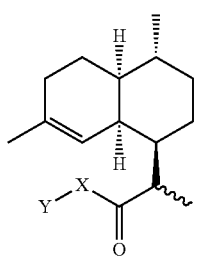

(I)

wherein
X is O, S, NH or NO
Y is a group selected from formulae (II), (III) and (IV)

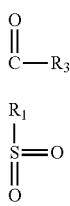

(II)

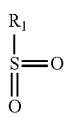

(III)

(IV)

$R_1$ and $R_2$, independently from each other, are hydrogen; a $C_1$-$C_{12}$ alkyl group which is linear or branched or a $C_3$-$C_{10}$ cycloalkyl group, said alkyl group being unsubstituted or substituted by one or more substituent(s) selected from a $C_1$-$C_6$ alkyl group and a halogen; a trifluoromethyl group; a cycloalkylalkyl group where cycloalkyl and alkyl are as defined above; a $C_2$-$C_{12}$ alkenyl group which is linear or branched, said alkenyl group being unsubstituted or substituted by one or more substituent(s) selected from a $C_1$-$C_6$ alkyl group and a halogen; a $C_5$-$C_{14}$ aryl or heteroaryl group, said aryl or heteroaryl group being unsubstituted or substituted by one or more substituent(s) selected from a $C_1$-$C_6$ alkyl group and a halogen; an arylalkyl group where aryl and alkyl are as defined above; or a heteroarylalkyl group where heteroaryl and alkyl are as defined above; and $R_3$ is $R_1$, $OR_1$, $NHR_1$ or $NR_1R_2$, where $R_1$ and $R_2$ are as defined above.

In some embodiments, the compounds of formula (I) are the diastereoisomers represented by formula (Ia)

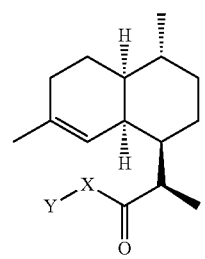

(Ia)

where X and Y are as defined above.

Among compounds of formulae (I) and (Ia), in some embodiments, the compounds are those in which X is an oxygen atom.

In some embodiments, the compounds of formulae (I) and (Ia) are those in which
X is O;
Y is a group selected from formulae (II), (III) and (IV)

(II)

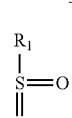

(III)

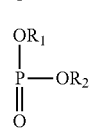

(IV)

$R_1$ and $R_2$, independently from each other, are hydrogen; a $C_1$-$C_{12}$ alkyl group which is linear or branched or a $C_3$-$C_{10}$ cycloalkyl group, said alkyl group being unsubstituted or substituted by one or more substituent(s) selected from a $C_1$-$C_6$ alkyl group and a halogen; a trifluoromethyl group; a $C_2$-$C_{12}$ alkenyl group which is linear or branched, said alkenyl group being unsubstituted or substituted by one or more substituent(s) selected from a $C_1$-$C_6$ alkyl group and a halogen; or a $C_5$-$C_{14}$ aryl or heteroaryl group, said aryl or heteroaryl group being unsubstituted or substituted by one or more substituent(s) selected from a $C_1$-$C_6$ alkyl group and a halogen; and $R_3$ is $R_1$, $OR_1$, $NHR_1$ or $NR_1R_2$, where $R_1$ and $R_2$ are as defined above.

In some embodiments, those compounds of formulae (I) and (Ia), are those wherein X is O;

Y represents a group of formula (II)

(II)

where $R_3$ is $OR_1$ and $R_1$ is a $C_1$-$C_{12}$ alkyl group which is linear or branched or a $C_3$-$C_{10}$ cycloalkyl group, said alkyl group being unsubstituted or substituted by one or more substituent(s) selected from a $C_1$-$C_6$ alkyl group and a halogen, or a $C_5$-$C_{14}$ aryl or heteroaryl group, and in some embodiments, a phenyl group, said aryl or heteroaryl group being unsubstituted or substituted by one or more substituent(s) selected from a $C_1$-$C_6$ alkyl group and a halogen.

The compounds of formula (I) or (Ia) can be prepared, for instance by esterification of dihydroartemisinic acid with, for example, a haloformate of formula Y—X—C(O)-hal, where hal is chlorine, fluorine or bromine and X and Y are as defined above, according to usual methods.

In some embodiments, X represents oxygen and Y represents a group of formula (II) as defined above where $R_3$ is $OR_1$ and $R_1$ is a $C_1$-$C_{12}$ alkyl group which is linear or branched or a $C_3$-$C_{10}$ cycloalkyl group, said alkyl group being unsubstituted or substituted by one or more substituent(s) selected from a $C_1$-$C_6$ alkyl group and a halogen, or a $C_5$-$C_{14}$ aryl or heteroaryl group, and in some embodiments, a phenyl group, said aryl or heteroaryl group being unsubstituted or substituted by one or more substituent(s) selected from a $C_1$-$C_6$ alkyl group and a halogen.

In some embodiments, the step of preparing the compound of formula (I) or (Ia) can be combined to the subsequent steps of preparing artemisinin, without isolating the compound of formula (I) or (Ia) as an intermediate compound.

Also provided is the use of the compounds of formula (I) or (Ia), as defined above, for preparing artemisinin.

The working examples set forth below illustrate the process and compounds according to the invention, but in no way limit the scope of the invention.

In the following experimental part, examples 1 to 10 relate to the preparation of dihydroartemisinic acid derivatives of formula (I) or (Ia), and examples 11-13 relate to the preparation of artemisinin starting from a dihydroartemisinic acid derivative of formula (I) or (Ia).

EXAMPLE 1

Synthesis of (3R)-dihydroarteannuin B methyl carbonate or (3R)-dihydroarteannuin B acid, methyl mixed carbonate

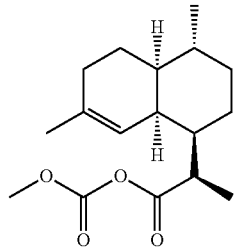 [SMILES: COC(=O)OC(=O)[C@H](C)[C@@H]1CC[C@@H](C)[C@@H]2CCC(C)=C[C@@H]21]

2.08 g (0.022 mol) of methyl chloroformate are added dropwise within 5 min, to a stirred solution of 5.04 g (0.021 mol) of DHAA and 2.43 g (0.024 mol) of triethylamine ($Et_3N$) in 25 mL toluene in an ice bath. After addition, stirring is continued for 20-30 min.

The mixture is then washed twice with water (2×100 mL) and dried over $MgSO_4$. The solution is then concentrated to dryness at reduced pressure and 5.18 g of an oily residue are obtained (crude yield=83.2%). The product can be used as such.

EXAMPLE 2

Synthesis of (3R)-dihydroarteannuin B acid, 2,2,2-trichloroethyl mixed carbonate

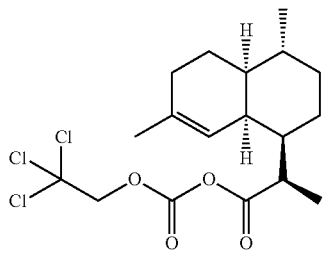 [SMILES: CC1=C[C@H]2[C@@H](CC1)[C@H](C)CC[C@H]2[C@@H](C)C(=O)OC(=O)OCC(Cl)(Cl)Cl]

4.72 g (0.022 mol) of 2,2,2-trichloroethyl chloroformate are added dropwise within 5 min. to a stirred solution of 5.07 g (0.021 mol) of DHAA and 2.43 g (0.024 mol) of $Et_3N$ in 25 mL toluene in an ice bath. After addition, stirring is continued for 20-30 min.

The mixture is then washed twice with water (2×100 mL) and dried over $MgSO_4$. The solution is then concentrated to dryness at reduced pressure and 8.39 g of an oily residue are obtained (crude yield=96.3%). The product can be used as such.

EXAMPLE 3

Synthesis of (3R)-dihydroarteannuin B acid, ethyl mixed carbonate

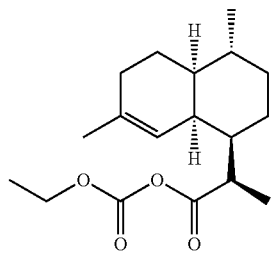 [SMILES: CCOC(=O)OC(=O)[C@H](C)[C@@H]1CC[C@@H](C)[C@@H]2CCC(C)=C[C@@H]21]

2.27 g (0.021 mol) of ethyl chloroformate are added dropwise within 5 min, to a stirred solution of 5.11 g (0.022 mol) of DHAA enriched in majority isomer and 3.42 g (0.025 mol)

of $K_2OC_3$ in 25 mL toluene in an ice bath. After addition, stirring is continued for 20-30 min.

The mixture is then washed twice with water (2×100 mL) and dried over $MgSO_4$. The solution is then concentrated to dryness at reduced pressure and 5.57 g of an oily residue are obtained (crude yield=85.4%). The product can be used as such.

$^1$H NMR (CDCl3, ppm): 5.08 (1H, s), 4.33 (2H, q, J=7.1 Hz), 2.58 (1H, m), 2.50 (1H, s), 1.95 (1H, m), 1.92 (1H, m), 1.82 (1H, m), 1.69 (1H, m), 1.64 (3H, s), 1.63 (2H, m), 1.54 (1H, m), 1.47 (1H, m), 1.37 (3H, t, J=7.1 Hz), 1.27 (1H, m), 1.24 (3H, d, J=7.0 Hz), 1.14 (1H, qd, J1=12.7 Hz, J2=3.2 Hz), 0.98 (1H, qd, J1=12.7 Hz, J2=3.2 Hz), 0.87 (3H, d, J=6.6 Hz);

$^{13}$C NMR (CDCl3, ppm): 14.0, 14.7, 19.7, 23.8, 25.7, 26.6, 27.3, 27.6, 35.1, 36.3, 41.7, 42.6, 43.7, 65.6, 118.9, 136.4, 149.3, 171.6;

MS: 308;

IR (cm$^{-1}$): 2924, 1816 and 1749, 1154, 997.

EXAMPLE 4

Synthesis of (3R/S)-dihydroarteannuin B acid, ethyl mixed carbonate (diastereomeric mixture)

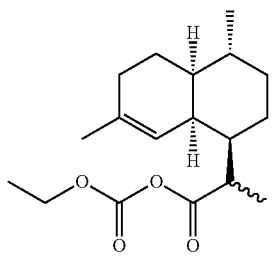 [SMILES: CCOC(=O)OC(=O)C(C)[C@@H]1CC[C@@H](C)[C@@H]2CCC(C)=C[C@@H]21]

2.27 g (0.021 mol) of ethyl chloroformate are added dropwise within 5 min. to a stirred solution of 5.11 g (0.022 mol) of the racemic DHAA and 2.45 g (0.024 mol) of N-methylmorpholine in 25 mL of toluene in an ice bath. After addition, stirring is continued for 20-30 min.

The mixture is then washed twice with water (2×100 mL) and dried over $MgSO_4$. The solution is then concentrated to dryness at reduced pressure and 6.11 g of an oily residue are obtained (crude yield=93.6%). The product can be used as such.

EXAMPLE 5

Synthesis of (3R)-dihydroarteannuin B acid, benzyl mixed carbonate

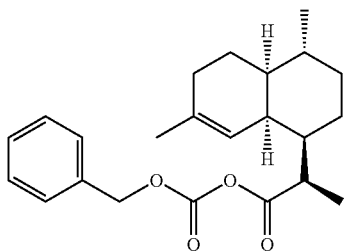 [SMILES: CC1=C[C@H]2[C@@H](CC1)[C@H](C)CC[C@H]2[C@@H](C)C(=O)OC(=O)OCc1ccccc1]

3.64 g (0.021 mol) of benzyl chloroformate are added dropwise within 5 min. to a stirred solution of 5.08 g (0.021 mol) of DHAA and 3.31 g (0.024 mol) of $K_2CO_3$ in 25 mL of dichloromethane in an ice bath. After addition, stirring is continued for 20-30 min.

The mixture is then washed twice with water (2×100 mL) and dried over $MgSO_4$. The solution is then concentrated to dryness at reduced pressure and 7.63 g of an oily residue are obtained (crude yield=97.4%). The product can be used as such.

EXAMPLE 6

Synthesis of (3R)-dihydroarteannuin B acid, phenyl mixed carbonate

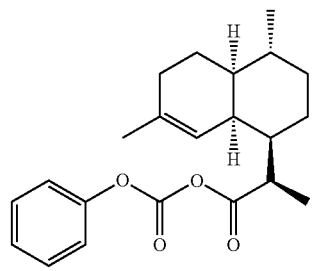 [SMILES: CC1=C[C@H]2[C@@H](CC1)[C@H](C)CC[C@H]2[C@@H](C)C(=O)OC(=O)Oc1ccccc1]

3.48 g (0.022 mol) of phenyl chloroformate are added dropwise within 5 min. to a stirred solution of 5.08 g (0.021 mol) DHAA and 3.36 g (0.024 mol) of $K_2CO_3$ in 25 mL of dichloromethane in an ice bath. After addition, stirring is continued for 20-30 min.

The mixture is then washed twice with water (2×100 mL) and dried over $MgSO_4$. The solution is then concentrated to dryness at reduced pressure and 6.85 g of an oily residue are obtained. This represents a crude yield of 90.8%. The product can be used as such.

EXAMPLE 7

Synthesis (3R)-dihydroarteannuin B acid, 1-chloroethyl mixed carbonate

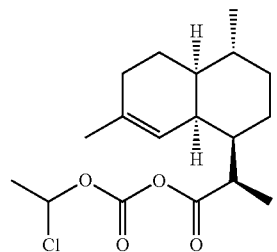 [SMILES: CC1=C[C@H]2[C@@H](CC1)[C@H](C)CC[C@H]2[C@@H](C)C(=O)OC(=O)OC(C)Cl]

3.02 g (0.021 mol) of 1-chloroethyl chloroformate are added dropwise within 5 min. to a stirred solution of 5.03 g (0.021 mol) of DHAA and 3.44 g (0.025 mol) of $K_2CO_3$ in 25 mL of dichloromethane in an ice bath. After addition, stirring is continued for 20-30 min.

The mixture is then washed twice with water (2×100 mL) and dried over $MgSO_4$. The solution is then concentrated to dryness at reduced pressure and 5.84 g of an oily residue are obtained (crude yield=80.5%). The product can be used as such.

EXAMPLE 8

Synthesis of (3R)-dihydroarteannuin B acid, propyl mixed carbonate

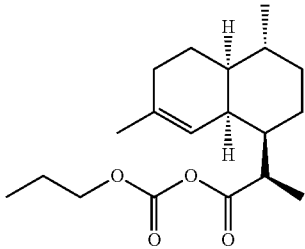 [SMILES: CCCOC(=O)OC(=O)[C@H](C)[C@@H]1CC[C@@H](C)[C@@H]2CCC(C)=C[C@@H]21]

2.62 g (0.021 mol) of propyl chloroformate are added dropwise within 5 min. to a stirred solution of 5.02 g (0.021 mol) DHAA and 4.22 g (0.031 mol) of $K_2OC_3$ in 25 mL dichloromethane in an ice bath. After addition, stirring is continued for 20-30 min.

The mixture is then washed twice with water (2×100 mL) and dried over $MgSO_4$. The solution is then concentrated to dryness at reduced pressure and 6.53 g of an oily residue are obtained (crude yield=95.7%). The product can be used as such.

EXAMPLE 9

Synthesis of (3R)-dihydroarteannuin B acid, 2,2,2-trichloro-1,1-dimethyl mixed carbonate

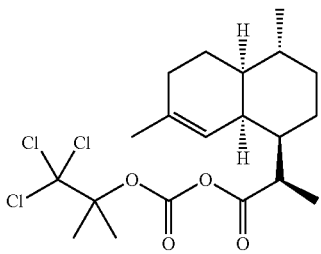 [SMILES: CC1=C[C@H]2[C@@H](CC1)[C@H](C)CC[C@H]2[C@@H](C)C(=O)OC(=O)OC(C)(C)C(Cl)(Cl)Cl]

5.08 g (0.021 mol) of 2,2,2-trichloro-1,1-dimethylethyl chloroformate is added dropwise within 5 min, to a stirred solution of 5.04 g (0.021 mol) DHAA and 3.85 g (0.028 mol) $K_2CO_3$ in 25 mL dichloromethane in an ice bath. After addition, stirring is continued for 20-30 min.

The mixture is then washed twice with water (2×100 mL) and dried over $MgSO_4$. The solution is then concentrated to dryness at reduced pressure and 8.52 g of an oily residue are obtained (crude yield=91.3%). The product can be used as such.

EXAMPLE 10

Synthesis of (3R)-dihydroarteannuin B acid, 2-chloroethyl mixed carbonate

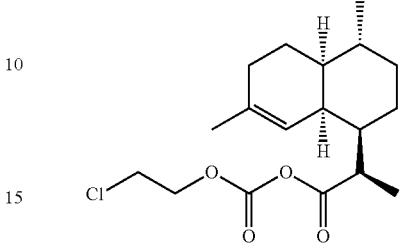

3.04 g (0.021 mol) of 2-chloroethyl chloroformate are added dropwise within 5 min. to a stirred solution of 5.01 g (0.021 mol) of DHAA and 4.04 g (0.029 mol) of $K_2OC_3$ in 25 mL of dichloromethane in an ice bath. After addition, stirring is continued for 20-30 min.

The mixture is then washed twice with water (2×100 mL) and dried over $MgSO_4$. The solution is then concentrated to dryness at reduced pressure and 6.78 g of an oily residue are obtained (crude yield=93.5%). The product can be used as such.

EXAMPLE 11

Synthesis of Artemisinin

An amount of 4 g of the dihydroartemisinic acid (DHAA) derivative of formula (I) or (Ia) prepared in examples 1 to 10 above (1 eq.), 0.01 eq. of tetraphenylporphyrin and 80 mL of methylene chloride are introduced at 20° C. in a clean 0.2 liter reactor, The mixture is then cooled down to −10° C. and air or oxygen is bubbled through the mixture (40-50 mL/min.) under stirring at 300-400 rpm. After 30 min., trifluoroacetic acid (TFA, 0.5 eq.) is added and a halogen lamp is switched on.

The mixture is stirred overnight (~19 h) at −10° C. and then warmed up to 10° C. (60 min.) and stirred at 10° C. during 60 min.

The mixture is then warmed up to 20° C. in about 60 min. and then the air introduction is stopped, the lamp switched off and the mixture stirred at 20° C. during 2 h.

Then, the reaction mixture is treated by addition of 20 mL of water then 20 mL of a solution of aqueous saturated $NaHCO_3$. The resulting mixture was then left for decantation and the two layers were separated. The organic layer is then loaded back in the vessel and washed again by addition of 20 mL of water then 20 mL of a solution of aqueous saturated $NaHCO_3$. After decantation and layers separation, the organic layer is washed with 20 ml of water.

After decantation, the organic layer is then concentrated under progressive vacuum at 30° C. using a rotary evaporator. The dry product crystallizes at room temperature. Then 12 mL of n-heptane are added and the mixture is stirred during 1 h at 20° C.

The reaction mixture is then filtrated under Buchner funnel (n° 3). The wet solid is then washed first with 8 mL and then with 12 mL of n-heptane.

The wet solid is then dried under vacuum at 40° C. overnight (~15 h).

Crude artemisinin is obtained with good titrated yield (62% ti/ti).

If desired, an additional recrystallization step in an ethanol/water mixture (70/30) can be performed on the solid product precipitated in n-heptane. The artemisinin thus obtained has an excellent purity and a recrystallization yield higher than 90%.

EXAMPLE 12

Synthesis of Artemisinin

A solution of mixed carbonate derivative of formula (I) or (Ia) prepared in example 3 above (100 g, 1 eq.) in dichloromethane (550 mL), and 0.00031 eq. of tetraphenylporphyrin are introduced at 20° C. in a clean reactor.

The mixture is then cooled down to −10° C. and air or oxygen is bubbled through the mixture (260-300 mL/min.) under stirring at 200 rpm. After 30 min., the mercury lamp is switched on and trifluoroacetic acid (TFA, 0.5 eq.) is added.

The mixture is stirred for 7 hours at −10° C. and the air introduction is stopped, the lamp switched off.

The reaction mixture is then warmed up to 20° C. over 30 min. and stirred at 20° C. during 2 hours.

Then, the reaction mixture is treated by addition of 200 mL of water then 200 mL of a solution of aqueous saturated NaHCO$_3$. The resulting mixture was then left for decantation and the two layers were separated. The organic layer is then loaded back in the vessel and washed again by addition of 200 mL of water then 200 mL of a solution of aqueous saturated NaHCO$_3$. After decantation and layers separation, the organic layer is washed with 200 ml of water.

After decantation, organic layer is then concentrated under progressive vacuum at 30° C. using a rotary evaporator. The dry product crystallizes at room temperature. Then 300 mL of n-heptane and 30 mL of ethyl alcohol are added. The resulting mixture is stirred during 1 hour at 50° C. The reaction mixture is cooled to 20° C. in 1 hour and is stirred at 20° C. during 30 minutes.

The reaction mixture is then filtrated under Buchner funnel (n° 3). The wet solid is then washed twice with 200 mL of n-heptane.

The wet solid is then dried under vacuum at 40° C. overnight (~15 h).

The yield of highly pure artemisinin obtained is 51% without the additional recrystallization step of Example 11.

EXAMPLE 13

Synthesis of Artemisinin

A solution of mixed carbonate derivative of formula (I) or (Ia) prepared in example 3 above (650 g—93% assay, 1 eq.) in dichloromethane (4 L), and 0.00027 eq. of tetraphenylporphyrin are introduced at 20° C. in a clean reactor.

The mixture is then cooled down to −10° C. and air or oxygen is bubbled through the mixture (900 mL/min.) under stirring. After 30 min., the mercury lamp is switched on and trifluoroacetic acid (TFA, 0.5 eq.) is added.

The mixture is stirred overnight at −10° C. The reaction mixture is then warmed up to 20° C. over 40 min and the air introduction is stopped, and the lamp switched off.

Then, the reaction mixture is treated by addition of 650 mL of water then 1300 mL of a solution of aqueous saturated NaHCO$_3$. The resulting mixture was then left for decantation and the two layers were separated. The organic layer is then loaded back in the vessel and washed again by addition of 650 mL of water then 650 mL of a solution of aqueous saturated NaHCO$_3$. After decantation and layers separation, the organic layer is finally washed with 1300 ml of water.

After decantation, the organic layer is then concentrated under progressive vacuum at 30° C. and 1950 mL of n-heptane was added. The concentration is pursued at constant volume to remove residual dichloromethane. 195 mL of ethyl alcohol was then added. The resulting mixture is stirred during 1 hour at 50° C. The reaction mixture is cooled to 20° C. in 2 hour and is stirred at 20° C. during 1 hour.

The reaction mixture is then filtrated under Buchner funnel (n° 3). The wet solid is then washed twice with 1300 mL of n-heptane.

The wet solid is then dried under vacuum at 40° C.

The yield of highly pure artemisinin obtained is 56% without the additional recrystallization step of Example 11.

The titrated yields of crude artemisinin obtained by using the activated DHAA derivatives (examples 1 to 10) are summarized in Table 1 below.

TABLE 1

| Example No | Name | Yields (% ti/ti) |
|---|---|---|
| 1 | (3R)-dihydroarteannuin B acid, methyl mixed carbonate | 62.2 |
| 2 | (3R)-dihydroarteannuin B acid, 2,2,2-trichloroethyl mixed carbonate | 58.7 |
| 3 | (3R)-dihydroarteannuin B acid ethyl mixed carbonate) | 62 |
| 5 | (3R)-dihydroarteannuin B acid benzyl mixed carbonate | 59.2 |
| 6 | (3R)-dihydroarteannuin B acid phenyl mixed carbonate | 58.4 |
| 8 | (3R)-dihydroarteannuin B acid propyl mixed carbonate | 54.5 |
| 10 | (3R)-dihydroarteannuin B acid 2-chloroethyl mixed carbonate | 54.9 |

The results show that the yields in artemisinin obtained by using the activated DHAA derivatives according to the present process are significantly higher than those obtained in the literature when using DHAA methyl esters in the prior art processes, such as described in Tetrahedron Lett 1993, 4435-4438, which discloses that the yield of artemisinin obtained amounts at most to 30%.

The invention claimed is:

1. A process for preparing artemisinin, comprising the steps of:
preparing a mixture comprising (i) a dihydroartemisinic acid derivative of formula (I)

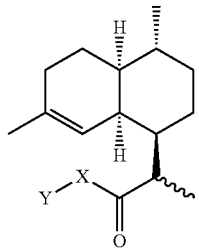

(I)

wherein
X is O
Y is formula (II)

(II)

R$_1$ is hydrogen; a C$_1$-C$_{12}$ alkyl group which is linear or branched or a C$_3$-C$_{10}$ cycloalkyl group, said alkyl group being unsubstituted or substituted by one or more substituent(s) selected from a $C_1$-$C_6$ alkyl group and a halogen; a trifluoromethyl group; a cycloalkylalkyl group where cycloalkyl and alkyl are as defined above; a $C_2$-$C_{12}$ alkenyl group which is linear or branched, said alkenyl group being unsubstituted or substituted by one or more substituent(s) selected from a $C_1$-$C_6$ alkyl group and a halogen; a $C_5$-$C_{14}$ aryl or heteroaryl group, said aryl or heteroaryl group being unsubstituted or substituted by one or more substituent(s) selected from a $C_1$-$C_6$ alkyl group and a halogen; an arylalkyl group where aryl and alkyl are as defined above; or a heteroarylalkyl group where heteroaryl and alkyl are as defined above;

$R_3$ is $OR_1$ where $R_1$ is as defined above;

(ii) at least one organic solvent and (iii) a photosensitizer, subjecting said mixture to photooxidation by means of a light source, and recovering the artemisinin thus obtained.

2. The process of claim 1, wherein the dihydroartemisinic acid derivative has the formula (Ia)

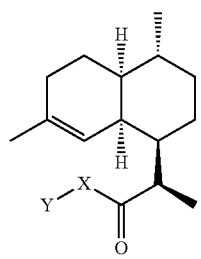

(Ia)

in which X and Y are as defined in claim 1.

3. The process according to claim 1 or 2, wherein the at least one organic solvent is selected from the group consisting of alcohols, chlorinated solvents, ketones, sulfoxides, nitriles, N,N-disubstituted amines, esters, nitrogenated heterocycles, ethers, alkanes, aromatic solvents, and mixtures thereof.

4. The process according to claim 1 or 2, wherein the at least one organic solvent is dichloromethane.

5. The process according to claim 1 or 2, wherein the organic solvent comprises a polar solvent and the polar solvent is used in a ratio of about 4 to 20 volumes with respect to the dihydroartemisinic acid derivative of formula (I) or (Ia).

6. The process according to claim 1 or 2, wherein the photosensitizer is selected from Rose bengal, tetraphenylporphyrin, tetraphenylporphyrin derivatives, tetramethylthionine chloride (methylene blue) and toluidine blue.

7. The process according to claim 1 or 2, wherein the photosensitizer is used in a molar ratio of about 0.000001 to 1 equivalent with respect to the dihydroartemisinic acid derivative of formula (I) or (Ia).

8. The process according to claim 1 or 2, wherein the mixture comprises an acid catalyst.

9. The process according to claim 8, wherein the acid catalyst is present in an amount of 0.5 equivalent per equivalent of compound of formula (I) or (Ia).

10. The process according to claim 8, wherein the acid catalyst is a protic acid.

11. The process according to claim 8, wherein the acid catalyst is trifluoroacetic acid.

12. The process according to claim 1 or 2, wherein it comprises the steps of:

preparing a mixture comprising (i) a dihydroartemisinic acid derivative of formula (I) or (Ia) as defined in claim 1 or 2, (ii) at least one organic solvent, and (iii) a photosensitizer at ambient temperature, cooling the reaction mixture to a temperature in the range of about −78° C. to ambient temperature with air or oxygen bubbling into it, adding a catalytic amount of an acid catalyst, switching the light source on, maintaining the reaction mixture at the same temperature for 3 h to 24 h, warming up the reaction mixture to a temperature in the range of about 5 to 15° C. for 2 to 4 hours, and then to a higher temperature in the range of about 15 to 25° C. for 1 to 3 hours, stopping the reaction, maintaining the reaction mixture at a temperature in the range of about 15° C. to 25° C. for 1 to 3 hours, and recovering the artemisinin thus obtained.

13. The process according to claim 12, wherein the acid catalyst is chosen from protic acids or Lewis acids.

14. The process according to claim 12, wherein:

the first cooling step is carried out at a temperature between −5° C. and −20° C.;

during the warming up step, the reaction mixture is warmed up to 10° C. for 2 h, and then to ambient temperature for 1 hour, or after stopping the reaction, the reaction mixture is maintained at ambient temperature for 2 h.

15. The process according to claim 12, further comprising further purifying the recovered artemisinin.

16. The process according to claim 1 or 2, wherein the artemisinin is recovered by precipitation and isolation in an alkane/alcohol mixture.

17. The process according to claim 16, wherein the alkane is selected from n-heptane, n-hexane, cyclohexane, n-pentane, and CMC; and the alcohol is selected from ethanol and isopropanol.

* * * * *